US010660583B2

(12) United States Patent
Haider

(10) Patent No.: US 10,660,583 B2
(45) Date of Patent: May 26, 2020

(54) PATIENT TRANSPORT SYSTEM

(71) Applicant: Siemens Aktiengesellschaft, Munich (DE)

(72) Inventor: Sultan Haider, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1102 days.

(21) Appl. No.: 14/849,942

(22) Filed: Sep. 10, 2015

(65) Prior Publication Data

US 2016/0066869 A1 Mar. 10, 2016

(30) Foreign Application Priority Data

Sep. 10, 2014 (DE) .................... 10 2014 218 119

(51) Int. Cl.
| | | |
|---|---|---|
| *A61B 6/04* | (2006.01) | |
| *A61N 5/10* | (2006.01) | |
| *A61B 5/055* | (2006.01) | |
| *A61B 6/10* | (2006.01) | |
| *A61B 5/00* | (2006.01) | |

(52) U.S. Cl.
CPC .......... *A61B 6/0457* (2013.01); *A61B 5/0555* (2013.01); *A61B 6/0407* (2013.01); *A61B 6/0492* (2013.01); *A61N 5/1049* (2013.01); *A61B 5/742* (2013.01); *A61B 5/7405* (2013.01); *A61B 6/102* (2013.01); *A61N 2005/105* (2013.01); *A61N 2005/1063* (2013.01); *A61N 2005/1097* (2013.01)

(58) Field of Classification Search
CPC ... A61B 6/0457; A61B 5/0555; A61B 6/0492; A61B 6/0407; A61B 5/7405; A61B 5/742; A61B 6/102; A61N 5/1049; A61N 2005/1097; A61N 2005/105; A61N 2005/1063; B25J 9/1697
See application file for complete search history.

(56) References Cited

U.S. PATENT DOCUMENTS

| | | | | |
|---|---|---|---|---|
| 2,818,553 A | * | 12/1957 | Jaffe | ............... G01S 1/02 340/904 |
| 3,861,807 A | * | 1/1975 | Lescrenier | ........... A61B 6/0457 356/139.07 |
| 5,262,852 A | * | 11/1993 | Eouzan | ................... G01S 3/784 348/148 |

(Continued)

FOREIGN PATENT DOCUMENTS

DE 102012213202 1/2014

*Primary Examiner* — Nicholas F Polito
*Assistant Examiner* — Alexis Felix Lopez
(74) *Attorney, Agent, or Firm* — Schiff Hardin LLP

(57) ABSTRACT

The patient transport system has a mobile patient transport device for docking at a medical device, an acquisition device for acquiring suitable information for docking, and a control device for docking control of the mobile patient transport device. An evaluation device is coupled to the acquisition device and used the information acquired by the acquisition device to establish a path of the patient transport device. An optical or acoustic designation device specifies the established path of the patient transport device by at least one optical marking and/or acoustic signals. The optical marking and/or the acoustic signals are detected and control information is derived therefrom.

16 Claims, 3 Drawing Sheets

(56) References Cited

U.S. PATENT DOCUMENTS

| | | | | |
|---|---|---|---|---|
| 5,825,305 A * | 10/1998 | Biferno | ............... | B64D 47/02 340/958 |
| 6,535,242 B1 * | 3/2003 | Strumolo | ............... | B60R 11/04 348/148 |
| 6,704,621 B1 * | 3/2004 | Stein | ............... | G01S 11/12 382/104 |
| 7,117,090 B2 * | 10/2006 | Haider | ............... | G06K 9/209 701/301 |
| 8,396,597 B2 * | 3/2013 | Anderson | ............... | G05D 1/0276 318/577 |
| 9,186,793 B1 * | 11/2015 | Meier | ............... | B25J 9/1694 |
| 9,814,432 B2 * | 11/2017 | Igney | ............... | A61B 6/0407 |
| 2006/0167356 A1 * | 7/2006 | Everett | ............... | A61B 5/0555 600/407 |
| 2006/0169288 A1 * | 8/2006 | Kleen | ............... | A61B 6/547 128/845 |
| 2009/0231582 A1 * | 9/2009 | Aebischer | ............... | G01C 15/002 356/364 |
| 2010/0316469 A1 * | 12/2010 | Lert | ............... | B65G 1/045 414/273 |
| 2011/0154569 A1 * | 6/2011 | Wiggers | ............... | A61B 6/0407 5/81.1 R |
| 2012/0029697 A1 | 2/2012 | Ota et al. | | |
| 2012/0185122 A1 * | 7/2012 | Sullivan | ............... | G05D 1/0272 701/23 |
| 2014/0094990 A1 * | 4/2014 | Hyde | ............... | A61G 1/0275 701/1 |
| 2014/0331406 A1 * | 11/2014 | Haider | ............... | A61G 7/08 5/600 |
| 2014/0335734 A1 * | 11/2014 | Koerth | ............... | A61G 7/05 439/626 |
| 2014/0357981 A1 * | 12/2014 | Dumoulin | ............... | A61B 5/0555 600/415 |
| 2014/0378816 A1 * | 12/2014 | Oh | ............... | G01R 33/283 600/409 |
| 2015/0057802 A1 * | 2/2015 | Kroyan | ............... | B25J 9/1684 700/259 |
| 2015/0277420 A1 * | 10/2015 | Heijman | ............... | H03K 17/975 700/275 |
| 2016/0011224 A1 * | 1/2016 | Pollack | ............... | G01N 35/04 700/230 |
| 2016/0082595 A1 * | 3/2016 | Feng | ............... | G05D 1/0234 700/259 |
| 2016/0157955 A1 * | 6/2016 | Torigoe | ............... | G06T 7/248 378/42 |
| 2016/0206491 A1 * | 7/2016 | Coppens | ............... | A61B 6/0407 |
| 2016/0361039 A1 * | 12/2016 | Wang | ............... | A61B 6/0407 |

* cited by examiner

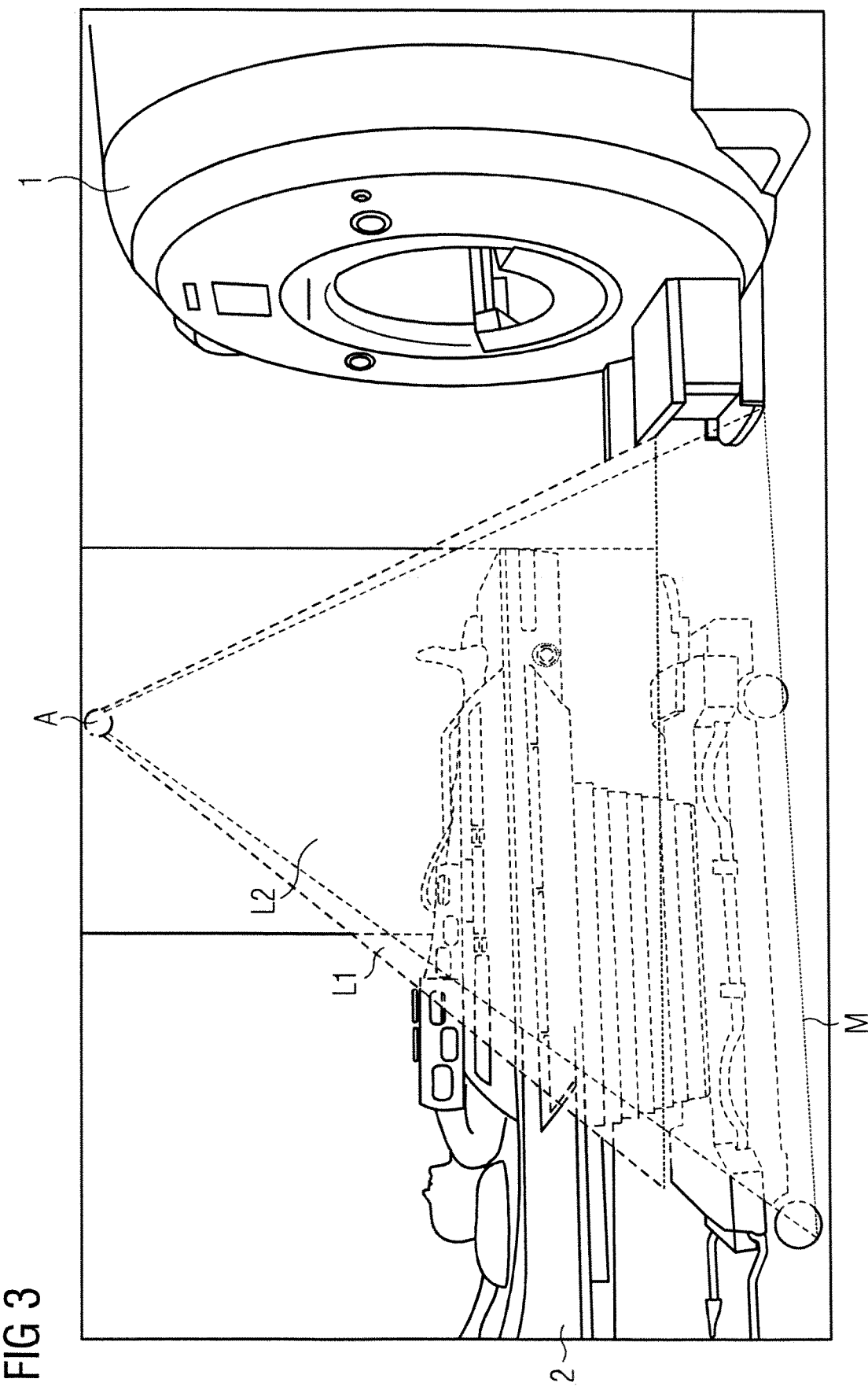

PATIENT TRANSPORT SYSTEM

BACKGROUND OF THE INVENTION

Field of the Invention

The invention concerns a patient transport system, and to a method for docking a mobile patient transport device belonging to the patient transport system.

Description of the Prior Art

In hospitals a patient transport device, e.g. a mobile patient table, also known as a trolley, that is able to be mechanically coupled to another device can be used for the transport of a patient from a treatment room to a magnetic resonance tomography (MRT) apparatus (for a neurological operation, for a cardiovascular intervention or for radiation therapy planning). In many hospitals or medical practices, however, a room in which there is an MRT apparatus is not always directly connected to the treatment room. This means that the trolley must be transported from one room to the other and when this is done it has to be decoupled in one room and connected or coupled to the MRT device in the other room. Because of space problems the trolley cannot be coupled directly to the MR bore (scanner) or the therapy system. Because of the mechanical requirements on the trolley and the weight of the patient, the trolley can be very heavy and easily uncoupled or not correctly coupled, which can lead to damage to the coupling system. This may possibly mean that an examination cannot take place.

Therefore a support system is needed that guides the trolley to the coupling system of the MR system or therapy system and couples it to such systems, in order to avoid damage to the coupling system.

The docking of a patient transport device to a medical device ideally should be done quickly and efficiently in order to keep the stress on the patient low and to not interrupt the medical workflow. A trolley is disclosed in the US 20060167356 A1 that provides automatic support for the docking process. The latching of the trolley to the medical device is assisted by sensors, in order to avoid operators from having difficulty in connecting the trolley and the medical device.

A patient transport device is described in DE 102013208610.5 that has a central fifth wheel that can be controlled in rotation around a vertical axis, to facilitated maneuverability of the transport device.

A movable device is known from U.S. Pat. No. 7,117,090 B2 to which a rotatable camera is attached that can record panoramic images around the device, so that potential collisions with obstacles can be prevented.

SUMMARY OF THE INVENTION

An object of the present invention is to provide support for operating personnel when patients are being transported by a patient transport system.

The object is achieved in accordance with the invention by a patient transport system having a mobile patient transport device embodied for docking at a medical device, an acquisition device that acquires information relevant to docking, and a control processor for docking control of the mobile patient transport device, and an evaluation processor coupled to the acquisition device that establishes, with the information acquired by the acquisition device, a path of the patient transport device for docking at the medical device, an optical or acoustic display device that designates, in a humanly perceptible manner, the established movement path of the patient transport device by at least one optical indicator and/or acoustic signals, and a further acquisition device that acquires the optical indicator and/or the acoustic signals and derives, from the acquired indicator and/or signals, at least one item of control information and that supplies this at least one item of control information to the control device. The control device then uses this at least one item of control information in the aforementioned docking control.

The medical device or a medical modality can be a computed tomography gantry, a magnetic resonance tomography scanner, x-ray device, a radiotherapy device, etc.

As noted, the patient transport system has at least one acquisition device for acquiring information that is relevant to docking. The term "information" in this case is to be understood as encompassing many individual contiguous or separate items of information. The information, for example, can involve an image.

The idea underlying the invention is that not only the docking process itself, but also the approach of the patient transport device to the docking interface of the medical device can be assisted. The present invention assists the operating personnel in bringing the transport device to the interface provided for docking, and thus facilitates further transport and docking for medical examinations or treatments.

The information acquired by the acquisition device can contain direction information, distance information, movement information or a combination of this information. It is likewise possible for the information to not directly contain one of these information types, but for direction information, distance information, movement information or a combination of this information to be obtained (derived) from the acquired information by evaluation (e.g. by analysis of an image recorded by a camera). Direction information, for example, would be the direction toward the docking interface of the medical device. Distance information would be the distance from the medical device. Movement information can be a movement created by a person moving or pushing the transport device that is detected.

The acquisition device is preferably formed with one or more sensors for detection of the information. This sensor can be an optical sensor (which is a term that encompasses a camera) capacitive sensor, a sensor based on ultrasound, or an RFID sensor.

The entire patient transport system can be embodied on the patient transport device. The acquisition device can then be formed of a number of sensors that are disposed, for example, on the front end and underneath the patient transport device.

In another embodiment, the acquisition device is not part of the patient transport device, but is disposed in the vicinity of the medical device. In this case, the acquisition device is in communication with a transmit device disposed externally from the patient transport device (the communication can be produced by a physical connection, but can also be a radio link). The transmit device is configured to send control information to the patient transport device. For this purpose, the patient transport device is equipped with a receiver that receives the control information sent by the transmit device. If processing or evaluation of the information acquired by the acquisition device is necessary, in these embodiments this can be achieved by an acquisition device also disposed externally of the patient transport device. Then an evaluation processor, which undertakes the necessary evaluation or analysis of the acquired information, is in communication with the acquisition device and transmit device also located externally of the patient transport device. This communication again need not necessarily be of a physical nature, but may be realized in a suitable way by wireless communication technology. The evaluation includes, for example, the calculation of a direction from a recorded image. The provision of the evaluation device externally of the patient transport device, in the case of magnetic resonance tomography, has the advantage that the externally situated evaluation device is easier to shield from magnetic fields.

In a further embodiment, the patient transport device is a trolley with a motor that drives the wheels of the trolley and controls its alignment. This motor can be designed to rotationally drive the wheels and/or for a height adjustment of the patient support. One motor or two separate motors can be provided for these respective functions.

The information acquired by the acquisition device can be a marking in the vicinity of the medical device or a camera image. The acquisition device is suitably disposed in accordance with the position and type of the information that is to be acquired. In an embodiment, at least one optical marking can be displayed on the floor as the designation, and the acquisition device can be attached to the patient transport device at a position such that the marking is able to be acquired by the acquisition device when the marking is located near the patient transport device in an acquisition area (field of view) of the acquisition device. Thus the acquisition device can be attached to the underside or to the side on one side or the other of the trolley.

The one or more optical markings can be displayed on the floor by a light beam emitted by the display device, particularly a laser beam. Preferably at least two light beams are sent out by the display device, which can be displayed on the floor in parallel to one another and spaced apart from one another in order to illuminate for the patient transport device a path to the medical device. In other words, the display device can illuminate a form of corridor for the trolley to facilitate the manual guidance of the trolley by the operating personnel, or the automatic, motor-driven guidance of the medical device.

The marking can be a line that allows a continuous detection of a path to the medical device. As an alternative, multiple separate markings can be provided. In such cases these markings are preferably spaced apart from one another so that in the acquisition area (area which is able to be detected by a sensor or a number of sensors of the acquisition device) at least one marking is always detected. Thus the markings can indicate a type of corridor for central guidance of the trolley within the corridor.

A further aspect of the invention is a method for docking a mobile patient transport device at a medical device, having the following steps.

Information suitable for docking is required.

The information is evaluated and a path of the patient transport device for docking at the medical device is established with the use of the evaluated information.

An optical and/or acoustic designation of the established path of the patient transport device is made by at least one optical indicator and/or acoustic signals.

The at least one optical indicator and/or of the acoustic signals is detected.

At least one item of control information is derived from the detected indicator and/or signals.

The mobile patient transport device is controlled on the basis of this control information.

The patient transport device can be controlled by motor drives.

Embodiments of the method correspond to the further developments of the above-described system.

The invention has the following advantages.

Damage to the docking system is avoided through improved guidance during docking.

Assistance to personnel during transport of a patient is provided with far less force being expended. The improved docking of the trolley leads to time savings.

The trolley can be used in medical practices or hospitals in which the therapy room is not directly adjacent to the room in which the medical device is located.

BRIEF DESCRIPTION OF THE DRAWINGS

FIG. 3 shows the inventive optical marking of the path that has been established.

DESCRIPTION OF THE PREFERRED EMBODIMENTS

Figure 1:
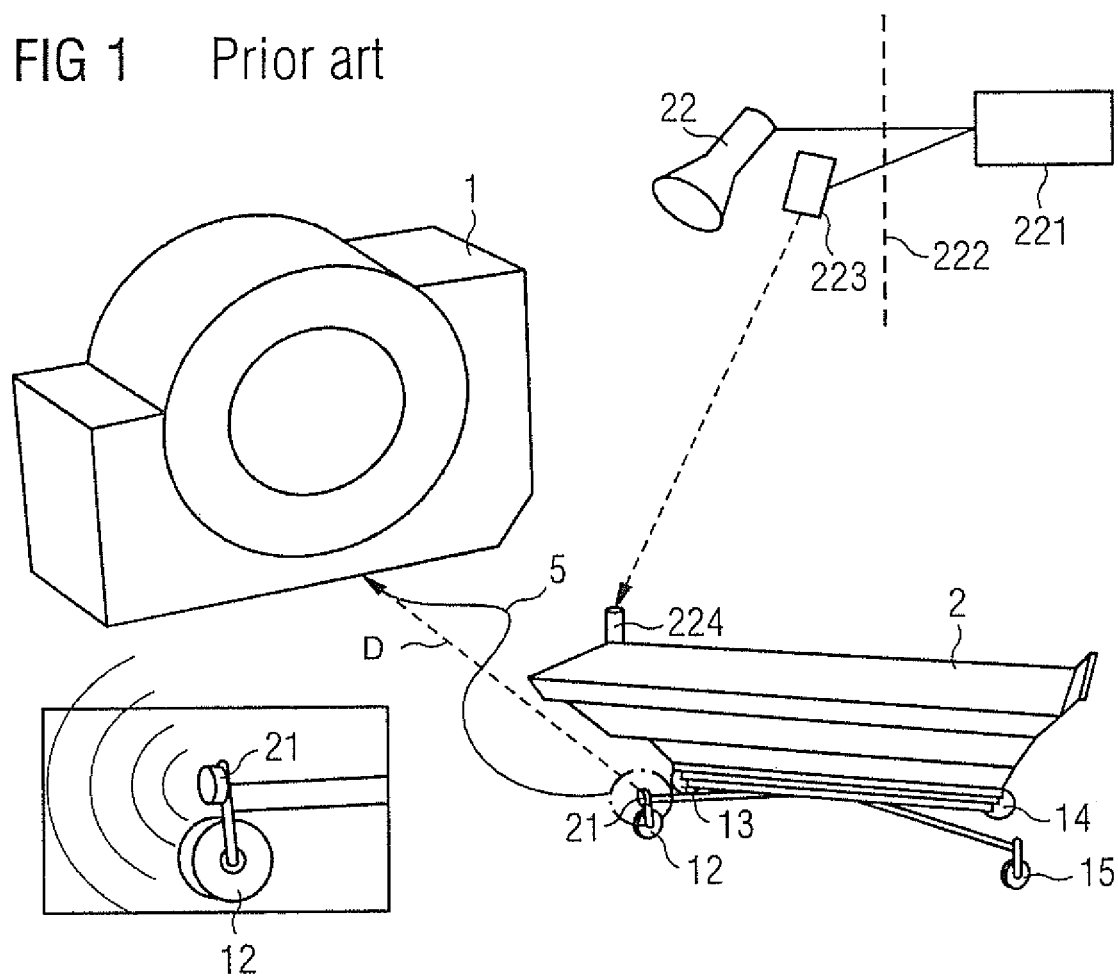
FIG. 1 shows the uncoupling and coupling of a trolley as described initially above.

FIG. 1 shows an example for a patient transport system. The patient transport device 2 shown is embodied for supporting the approach on a path 5 to the medical modality or medical device 1, The patient transport device has wheels 12, 13, 14 and 15. The acquisition device contains two subsystems, one of which is attached to the patient transport device 2 and the other is attached outside the patient transport device. The acquisition subsystem of the patient transport device 2 includes a sensor 21, which determines a distance D to the medical modality 1, by ultrasound for example. In addition, as an external acquisition system, a camera 22 attached close to the ceiling is provided which records an image of the patient transport device 2 and the modality 1. Said image is transmitted to an evaluation processor 221, which can be shielded from magnetic fields by shielding 222. It is also conceivable for a laser device not shown in the figure to be installed close to the camera 22 or to the sensor 223, which carries out a position detection of the trolley through a laser triangulation.

The evaluation processor 221 determines or calculates control information, e.g. a current proximity vector of the patient transport system 2 and its deviation from an ideal proximity vector. Control information is established by the evaluation processor 221 and is transmitted to a transmitter 223, which communicates the control information wirelessly to the receiver 224 of the patient transport device 2, so that, on the basis of this information, a control processor integrated into the transport device 2, which is not shown in the figure, can control or correct the path of the patient transport device.

Figure 2:
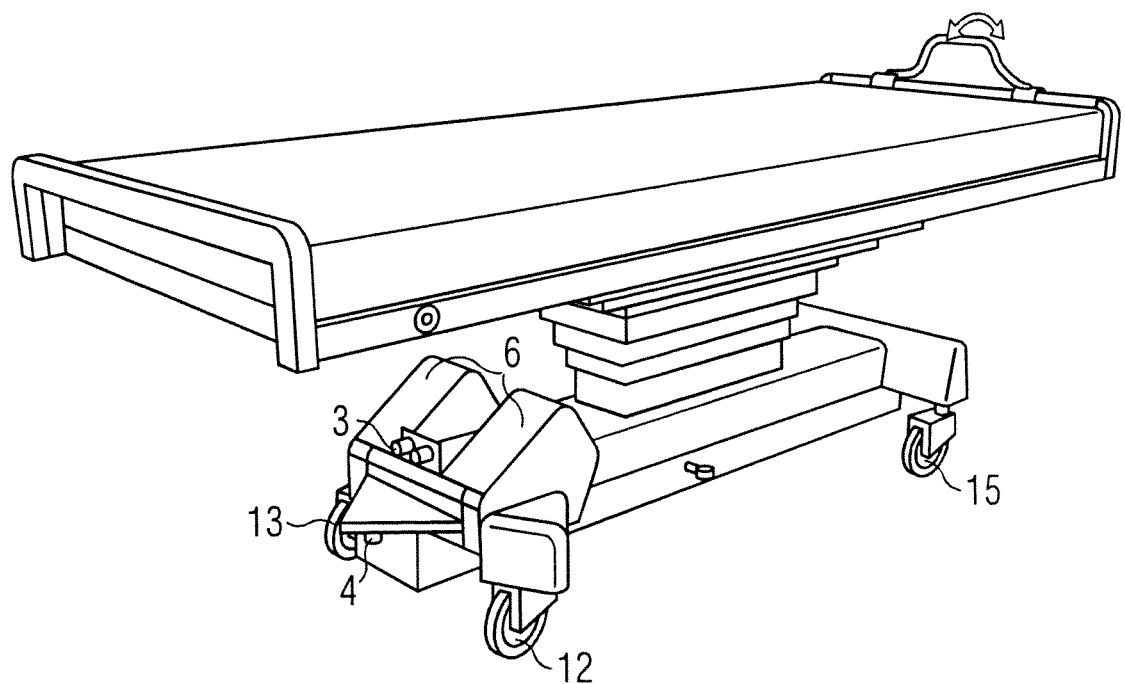
FIG. 2 shows an embodiment of the trolley in accordance with the invention.

FIG. 2 shows embodiments of the arrangement of the motor 6 supporting the movement of the trolley, a sensor 3 for distance measurement and thus to avoid a collision or for guidance to the docking system of the modality 1, and an embodiment of an optical sensor 4, which can support the following of a path.

Sensors can also be attached to the modality 1.

FIG. 3 shows a designation device A, preferably an emitter that emits light beams or emits at least one laser beam, which can be disposed in the vicinity of the camera 22 shown in FIG. 1. The information acquired by the acquisition device can be a marking in the vicinity of the medical device or of a camera image. The acquisition device is suitably disposed depending on the position and type of information to be acquired. In accordance with one embodiment at least one optical marking M can be designated on the floor and the acquisition device can be attached to the patient transport device such that the marking is able to be acquired by the acquisition device when it is close to the patient transport device in an acquisition area of the acquisition device. Thus the acquisition device can be attached to the underside or to the side on the one and/or the other side of the trolley.

The one or more optical markings M through at least one light beam emitted by the display device, especially at least one laser beam, can be displayed on the floor. Preferably at least two light beams L1 and L2 are emitted by the designation device A, which can be displayed on the floor in parallel to one another and spaced apart from one another in order to illuminate a path to the medical device for the patient transport device. In other words the designation device A can illuminate a type of corridor for the trolley 2 in order to facilitate the manual guidance of the trolley by the operating personnel or the automatic motor-driven guidance to the medical device.

The marking can consist of a line which allows a continuous acquisition of a path to the medical device. As an alternative a plurality of separate markings is provided. In such cases these markings are preferably spaced apart such that in the acquisition area (area which is able to be detected by a sensor or a number of sensors of the acquisition device), at least one marking is always detected. Thus the markings can indicate a type of corridor for central guidance of the trolley within the corridor.

The marking M need not be reproduced optically, but rather acoustically by (sound) signals. Thus different sound levels or sound frequencies can signal to the operating personnel the distance to the modality 1.

In order to follow the path displayed by the light beams, the patient transport device can also be switched into the type of auto-pilot mode, wherein the sensors detect the optical marking or the corridor illuminated by the light beams. This auto-pilot mode could be displayed on the patient transport device by means of a lamp or diode attached thereto.

Although modifications and changes may be suggested by those skilled in the art, it is the intention of the inventor to embody within the patent warranted hereon all changes and modifications as reasonably and properly come within the scope of his contribution to the art.

I claim as my invention:

1. A patient transport system comprising:
    a mobile patient transport device configured to dock with a medical apparatus;
    a first acquisition device configured to acquire docking information that is relevant to docking said patient transport device with said medical apparatus;
    a control computer configured to automatically control said docking of said mobile patient transport device with said medical apparatus;
    an evaluation processor in communication with said first acquisition device, said evaluation processor being configured to use said docking information acquired by said first acquisition device to establish a path between said patient transport device and said medical apparatus for docking said patient transport device with said medical apparatus;
    an optical designation device that is positioned at a location that is separate and detached from the patient transport device and the path of said patient transport device for docking with said medical apparatus, the optical designation device emitting a humanly-perceptible designation to indicate an entirety of said path established by said evaluation processor, said humanly-perceptible designation being an optical marking in an environment of said mobile transport device between said mobile transport device and said medical apparatus, the optical marking being comprised of at least two light beams that are formed parallel with one another to illuminate the entirety of said path as a corridor between said patient transport device and said medical apparatus;
    a second acquisition device configured to detect said humanly-perceptible designation and to derive control information therefrom, and to communicate said control information to said control computer; and
    said control computer being configured to control docking of said mobile patient transport device with said medical apparatus dependent on said control information.

2. A patient transport system as claimed in claim 1 wherein said first acquisition device is configured to acquire said docking information from the group consisting of direction information, distance information, and movement information.

3. A patient transport system as claimed in claim 1 wherein said first acquisition device is configured to detect at least one of a direction, a distance, and a movement between said mobile patient transport device and said medical apparatus, and to derive said docking information from at least one of the detected direction, distance, and movement.

4. A patient transport system as claimed in claim 1 wherein said first acquisition device is a sensor that detects said docking information.

5. A patient transport system as claimed in claim 1 wherein said first acquisition device is mounted on said mobile patient transport device.

6. A patient transport system as claimed in claim 1 wherein said first acquisition device is mounted adjacent said medical apparatus and has a field of view that encompasses said medical apparatus and said mobile patient transport device during said docking.

7. A patient transport system as claimed in claim 1 comprising multiple first acquisition devices that each acquires said docking information.

8. A patient transport system as claimed in claim 1 comprising multiple second acquisition devices that each detect said humanly-perceptible designation and derive said control information therefrom.

9. A patient transport system as claimed in claim 1 wherein said mobile patient transport device comprises a motor, and
    wherein said control computer is configured to operate said motor to control said docking dependent on said control information.

10. A patient transport system as claimed in claim 1 wherein said optical marking is emitted onto a floor on which said mobile patient transport device moves during said docking, and
    wherein said first acquisition device and said second acquisition device are mounted to said mobile patient transport device, and
    wherein said second acquisition device is configured with a field of view in which said optical marking is detected during said docking.

11. A patient transport system as claimed in claim 10 wherein said optical marking is emitted as a light beam.

12. A patient transport system as claimed in claim 11 wherein said optical designation device emits said light beam as a laser beam.

13. A patient transport system as claimed in claim 1, wherein the evaluation processor is shielded from magnetic fields.

14. A patient transport system as claimed in claim 1, wherein at least one of the first acquisition device and the second acquisition device includes a camera.

15. A method for docking a mobile transport device at a medical apparatus comprising:
moving a mobile patient transport device toward a medical apparatus;
with a first acquisition device, acquiring docking information that is relevant to docking said patient transport device with said medical apparatus;
with a control computer, automatically controlling said docking of said mobile patient transport device with said medical apparatus;
in an evaluation processor in communication with said first acquisition device, using said docking information acquired by said first acquisition device to establish a path between said patient transport and said medical apparatus for docking said patient transport device with said medical apparatus;
from an optical designation device that is positioned at a location that is separate and detached from the patient transport device and the path of said patient transport device for docking with said medical apparatus, emitting a humanly perceptible designation to indicate an entirety of said path established by said evaluation processor, said humanly-perceptible designation being an optical marking in an environment of said mobile transport device between said mobile transport device and said medical apparatus, the optical marking being comprised of at least two light beams that are formed parallel with one another to illuminate the entirety of said path as a corridor between said patient transport device and said medical apparatus;
with a second acquisition device, detecting said humanly-perceptible designation and deriving control information therefrom, and communicating said control information to said control computer; and
with said control computer, controlling docking of said mobile patient transport device with said medical apparatus dependent on said control information.

16. A method as claimed in claim 15 wherein said patient transport device comprises a motor drive, and wherein said method comprises controlling operation of said motor drive from said control computer dependent on said control information.

* * * * *